United States Patent
Mütze et al.

(10) Patent No.: US 8,955,918 B2
(45) Date of Patent: Feb. 17, 2015

(54) METHOD AND APPARATUS FOR INCREASING THE YIELD IN A DEPOSIT

(75) Inventors: Thomas Mütze, Freiberg (DE); Silke Röntzsch, Großröhrsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 106 days.

(21) Appl. No.: 13/702,626

(22) PCT Filed: Mar. 29, 2011

(86) PCT No.: PCT/EP2011/054767
§ 371 (c)(1),
(2), (4) Date: Dec. 7, 2012

(87) PCT Pub. No.: WO2011/154168
PCT Pub. Date: Dec. 15, 2011

(65) Prior Publication Data
US 2013/0082506 A1    Apr. 4, 2013

(30) Foreign Application Priority Data

Jun. 7, 2010 (EP) ..................... 10165033

(51) Int. Cl.
*E21C 39/00* (2006.01)
*E21B 43/295* (2006.01)
(Continued)

(52) U.S. Cl.
CPC .............. *E21B 43/295* (2013.01); *E21C 39/00* (2013.01); *E21B 21/065* (2013.01); *E21B 21/07* (2013.01);
(Continued)

(58) Field of Classification Search
CPC .............................. E21C 39/00; G01N 37/005
USPC .......................... 299/7, 18; 73/152.02, 152.03
See application file for complete search history.

(56) References Cited

U.S. PATENT DOCUMENTS

| 2,082,329 | A | 6/1937 | Foran et al. ...................... 175/48 |
| 2,167,393 | A | 7/1939 | Muncy ............................ 175/49 |

(Continued)

FOREIGN PATENT DOCUMENTS

| CN | 1643233 A | 7/2005 | ............. E21B 21/08 |
| CN | 2919251 Y | 7/2007 | ............. G01N 15/00 |

(Continued)

OTHER PUBLICATIONS

International Search Report and Written Opinion, Application No. PCT/EP2011/054767, 13 pages, May 11, 2011.

(Continued)

*Primary Examiner* — David Bagnell
*Assistant Examiner* — Michael Goodwin
(74) *Attorney, Agent, or Firm* — King & Spalding L.L.P.

(57) ABSTRACT

A method is provided for increasing the yield in a deposit comprising a rock that includes a valuable mineral, which can be exposed by virtue of the rock being comminuted, and at least one further mineral, wherein the valuable mineral has a higher density than the at least one further mineral, which method includes: carrying out a drilling operation using a drilling tool prior to the rock being extracted, drillings being generated in the process; forming an aerosol comprising the drillings and a gas stream; transferring the aerosol from the drilling tool to at least one air separator; carrying out hydraulic classification, wherein at least two fractions comprising in each case equal-falling particles of the drillings are formed; and determining a property which belongs to at least one of the fractions and is used as a measure for setting an optimum degree of comminution of the rock.

19 Claims, 4 Drawing Sheets

(51) Int. Cl.
*E21B 21/06* (2006.01)
*E21B 21/07* (2006.01)
*E21B 49/00* (2006.01)
*G01N 15/02* (2006.01)
*E21B 43/34* (2006.01)
*G01N 1/22* (2006.01)
*G01N 15/00* (2006.01)

(52) U.S. Cl.
CPC .......... *E21B 49/005* (2013.01); *G01N 15/0205* (2013.01); *E21B 43/34* (2013.01); *G01N 2001/2223* (2013.01); *G01N 2015/0019* (2013.01)
USPC .......................................................... 299/18

(56) References Cited

U.S. PATENT DOCUMENTS

| | | | |
|---|---|---|---|
| 3,528,514 A | 9/1970 | Sandvig | 175/49 |
| 3,645,131 A | 2/1972 | Turner et al. | 73/152.04 |
| 3,887,020 A | 6/1975 | Chaffin | 175/206 |
| 3,968,845 A | 7/1976 | Chaffin | 175/60 |
| 4,098,698 A | 7/1978 | Lamothe | 210/309 |
| 4,633,712 A * | 1/1987 | Scieszka | 73/866 |
| 6,301,953 B1 | 10/2001 | Zamfes | 73/38 |
| 6,453,727 B1 | 9/2002 | Lenormand et al. | 73/38 |
| 6,904,981 B2 | 6/2005 | Van Riet et al. | 175/66 |
| 7,980,329 B2 | 7/2011 | Spiecker et al. | 175/206 |
| 8,042,753 B2 * | 10/2011 | Yamaguchi et al. | 241/101.74 |
| 8,240,480 B2 | 8/2012 | Shaw et al. | 209/11 |
| 2003/0182997 A1 | 10/2003 | Williams | 73/152.23 |
| 2005/0087018 A1 | 4/2005 | Zamfes | 73/601 |
| 2006/0107772 A1 | 5/2006 | Shinn, II et al. | 73/864.43 |
| 2007/0137293 A1 | 6/2007 | Pop et al. | 73/152.23 |
| 2008/0202811 A1 * | 8/2008 | Zamfes | 175/46 |
| 2009/0302141 A1 | 12/2009 | Yamaguchi et al. | 241/33 |
| 2010/0000055 A1 | 1/2010 | Poulakis | 24/30.5 R |

FOREIGN PATENT DOCUMENTS

| | | | |
|---|---|---|---|
| CN | 101395336 A | 3/2009 | E21B 21/01 |
| CN | 101553323 A | 10/2009 | B06C 5/342 |
| DE | 10008106 A1 | 8/2001 | E21B 49/00 |
| DE | 10116363 A1 | 10/2002 | E21B 47/00 |
| RU | 2268364 C2 | 1/2006 | E21B 49/00 |
| WO | 2009/105469 A2 | 8/2009 | E21B 43/34 |
| WO | 2010/000055 A1 | 1/2010 | E21B 21/06 |
| WO | 2011/154168 A1 | 12/2011 | E21B 21/06 |
| WO | 2011/154169 A1 | 12/2011 | E21B 21/07 |
| WO | 2011/154170 A1 | 12/2011 | E21B 21/06 |

OTHER PUBLICATIONS

International Search Report and Written Opinion, Application No. PCT/EP2011/054769, 13 pages, May 11, 2011.
International Search Report and Written Opinion, Application No. PCT/EP2011/054771, 24 pages, Jul. 4, 2011.
Australian Office Action, Application No. 2011264085, 3 pages, Jun. 2, 2014.
Chinese Office Action, Application No. 2011800283838, 12 pages, Jun. 30, 2014.
Holmes, Ralph J., "Correct Sampling and Measurement—the Foundation of Accurate Metallurgical Accounting," Chemometrics and Intelligent Laboratory Systems, vol. 74, Elsevier Science Publishers, 14 pages, Mar. 12, 2004.
Australian Office Action, Application No. 2011264086, 3 pages, Oct. 1, 2013.
Australian Office Action, Application No. 2011264084, 3 pages, Mar. 11, 2014.
Australian Office Action, Application No. 2011264085, 2 pages.

* cited by examiner

METHOD AND APPARATUS FOR INCREASING THE YIELD IN A DEPOSIT

CROSS-REFERENCE TO RELATED APPLICATIONS

This application is a U.S. National Stage Application of International Application No. PCT/EP2011/054767 filed Mar. 29, 2011, which designates the United States of America, and claims priority to EP Patent Application No. 10165033.1 filed Jun. 7, 2010 The contents of which are hereby incorporated by reference in their entirety.

TECHNICAL FIELD

The disclosure relates to a method and an apparatus for increasing the yield in a deposit comprising a rock which comprises a valuable mineral which is to be exposed as a result of the rock being comminuted, and at least one further mineral, wherein the valuable mineral has a higher density than the at least one further mineral.

BACKGROUND

In order to exploit a deposit efficiently, the valuable mineral contained in the rock must be exposed and separated off as completely as possible. Different degrees of comminution of the rock are required for exposure of the valuable mineral depending on the mineral grain size thereof. A rock containing minerals having a high grain size must therefore be comminuted less to expose the valuable mineral than a rock containing minerals having a smaller grain size.

The "mineral grain size" of the valuable mineral is taken here to mean not the grain size of the crystallites of this mineral but the local spatial extent of the phase of valuable mineral in the rock.

Previously the extracted rock was comminuted to a mean mineral grain size, with a first part of the rock which comprises a valuable mineral having a high grain size being comminuted to an unnecessary extent, and a second part of the rock which comprises a valuable mineral having a smaller grain size being insufficiently comminuted. The unnecessarily intensive comminution of the first part of the rock leads to an unnecessarily high consumption of energy for the comminution operation. By contrast, the insufficient comminution of the second part of the rock leads to inadequate exposure, and consequently to inadequate separability of the valuable mineral, and therefore to ineffective exploitation of the deposit.

The mineral grain size and the distribution of minerals in a rock were previously determined in a time-consuming manner in that rock samples are taken at various sites in a deposit and analyzed. Approximately first-sized lumps of rock are collected in deposits for this purpose and/or exploration drilling operations are carried out in a coarse grid to obtain cores which can be evaluated. These rock samples are analyzed in the laboratory with respect to their mineralogical and chemical composition. While the chemical analysis substantially determines the type and extent of the elements present, the type and extent of the minerals present and their spatial arrangement is determined in the mineralogical analysis. The rock samples are partially ground in the direction of defined spatial axes in order to determine the spatial arrangement of the minerals. The spatial arrangement and distribution of the minerals in the rock may be discerned by way of optical analysis of the thin or ground sections, under a microscope for example. A spatially widely distributed arrangement of the minerals is associated with a low grain size of the minerals, while agglomerations of minerals at certain locations are associated with a higher mineral grain size.

Only a small amount of information may thus be provided with respect to the structure of a deposit or the spatial mineral grain size distribution of the valuable mineral in the deposit, and this information can only be provided after a considerable delay.

Deposit modeling, i.e. creation of a model of the deposit comprising the three-dimensional recording of layers of rock or rock formations with different grain sizes of the valuable mineral, is possible only to a limited extent due to the small amount of information available. Extraction and comminution of the rock geared toward the rock that is present locally, i.e. its valuable mineral content and the grain size thereof, is therefore possible only to a limited extent.

WO 2010/000055 A1 discloses a method and a device for, in particular continuous, on-site analysis of drilling cuttings from drilling mud. A sample of the drilling cuttings which is representative of the rock formation being drilled is taken and analyzed with respect to the type of rock and the chemical composition. Drilling parameters, comprising the drilling depth, gamma radiation emissions and/or additional parameters are optionally also logged and correlated with the results of the sample analysis.

SUMMARY

In one embodiment, a method is provided for increasing the yield in a deposit comprising a rock which comprises a valuable mineral which is to be exposed as a result of the rock being comminuted, and at least one further mineral, wherein the valuable mineral has a higher density than the at least one further mineral, the method including: carrying out a drilling operation using a drilling tool prior to the rock being extracted, drillings being generated in the process; forming an aerosol comprising the drillings and a gas stream; transferring the aerosol from the drilling tool to at least one air separator; carrying out a hydraulic classification, wherein at least two fractions comprising in each case equal-falling particles of the drillings are formed; and determining a property belonging to at least one of the fractions and used as a measure for setting an optimum degree of comminution of the rock.

In a further embodiment, an ore mineral is exposed as the valuable mineral by comminution of the rock. In a further embodiment, a particle size analysis is carried out on the equal-falling particles of the fractions, wherein in at least one of the fractions at least two particle fractions with different mean particle sizes are obtained which are separated from one another by gap grading, wherein the particle sizes d of a first particle fraction are proportional to a local mineral grain size of the valuable mineral in the rock and are used as a measure for setting the optimum degree of comminution of the rock. In a further embodiment, in the case where particle size analyses of at least two fractions in each case exhibit gap grading, the particle sizes d of the first particle fraction are used as a measure which originates from that fraction in which gap grading is the greatest. In a further embodiment, the particle size analysis is carried out using an optical analysis. In a further embodiment, the optical analysis of the equal-falling particles of the fractions takes place during their fall.

In a further embodiment, a depth of a drill bit of the drilling tool and/or position data concerning the position of the drilling tool in the deposit are acquired during the drilling operation and are logically linked to the measure, determined at this location, for the purpose of setting the optimum degree of comminution of the rock, and in that rock extracted at this location is comminuted according to the determined measure. In a further embodiment, at least one predefined drilling parameter and at least one measured value characterizing a current drilling behavior of the drilling tool are acquired, a dependency of the at least one measured value on the at least one drilling parameter being eliminated computationally, and in that at least one resulting rock-texture-dependent characteristic value is used as a further measure for setting an optimum degree of communication of the rock. In a further embodiment, the at least one drilling parameter is formed from a pressure of the drill bit of the drilling tool and/or a rotational speed of the drill bit and/or a gas volume flow of the gas stream for forming the aerosol and/or an impact frequency of the drill bit and/or a previous period of use of the drill bit and/or material or geometric data of the drill bit. In a further embodiment, the at least one measured value characterizing the current drilling behavior is chosen from the group of measured values comprising a drill speed, a resulting torque on the top drive of the drill bit, a gas pressure of the gas stream for forming the aerosol, an energy input into the drilling tool, and a vibration behavior of a drill pipe of the drilling tool. In a further embodiment, the determined property is also used to control a blasting operation and/or a conveying operation and/or a material management operation in the region of the deposit.

In another embodiment, an apparatus for carrying out any of the methods disclosed above may include: at least one comminution machine for comminuting the rock, wherein a degree of comminution of the rock can be changed; at least one control and/or regulating unit for setting the optimum degree of comminution at the at least one comminution machine; at least one drilling tool; at least one unit, for providing the gas stream, which is connected by way of at least one gas line to the at least one drilling tool; at least one air separator per drilling tool which is connected to the at least one drilling tool by way of at least one aerosol line; at least one device for determining at least one property of the fractions; and at least one computing unit for acquiring the at least one determined property of the fractions which forms the measure for determining the optimum degree of comminution, and optionally for transmitting at least one manipulated variable, determined on the basis of the measure, to the at least one control and/or regulating unit for setting the optimum degree of comminution at the at least one comminution machine.

In a further embodiment, the at least one computing unit is also configured to acquire the at least one drilling parameter and/or the at least one measured value at the drilling tool. In a further embodiment, the at least one computing unit is also configured to computationally eliminate a dependency of the at least one measured value, characterizing a current drilling behavior of the drilling tool, on the at least one drilling parameter and to calculate the at least one rock-texture-dependent characteristic value which forms a further measure for determining the optimum degree of comminution. In a further embodiment, the at least one computing unit is also configured to determine the manipulated variable on the basis of the measure and the further measure. In a further embodiment, the at least one computing unit is also configured to use the determined property additionally to control a blasting operation and/or conveying operation and/or a material management operation in the region of the deposit. In a further embodiment, the at least one air separator and the at least one device for determining at least one property of the fractions are arranged in the immediate vicinity of the drilling tool, in particular on the drilling tool. In a further embodiment, the at least one air separator is a cross-flow separator. In a further embodiment, at least one structure-borne noise sensor for detecting a vibration behavior of the drill pipe of the drilling tool is present on the at least one drilling tool. In a further embodiment, the device also comprises an extraction tool for the rock. In a further embodiment, the drilling tool and/or the extraction tool comprise/comprises at least one GPS unit.

BRIEF DESCRIPTION OF THE DRAWINGS

Example embodiments will be explained in more detail below with reference to figures, in which.

DETAILED DESCRIPTION

Figure 1:
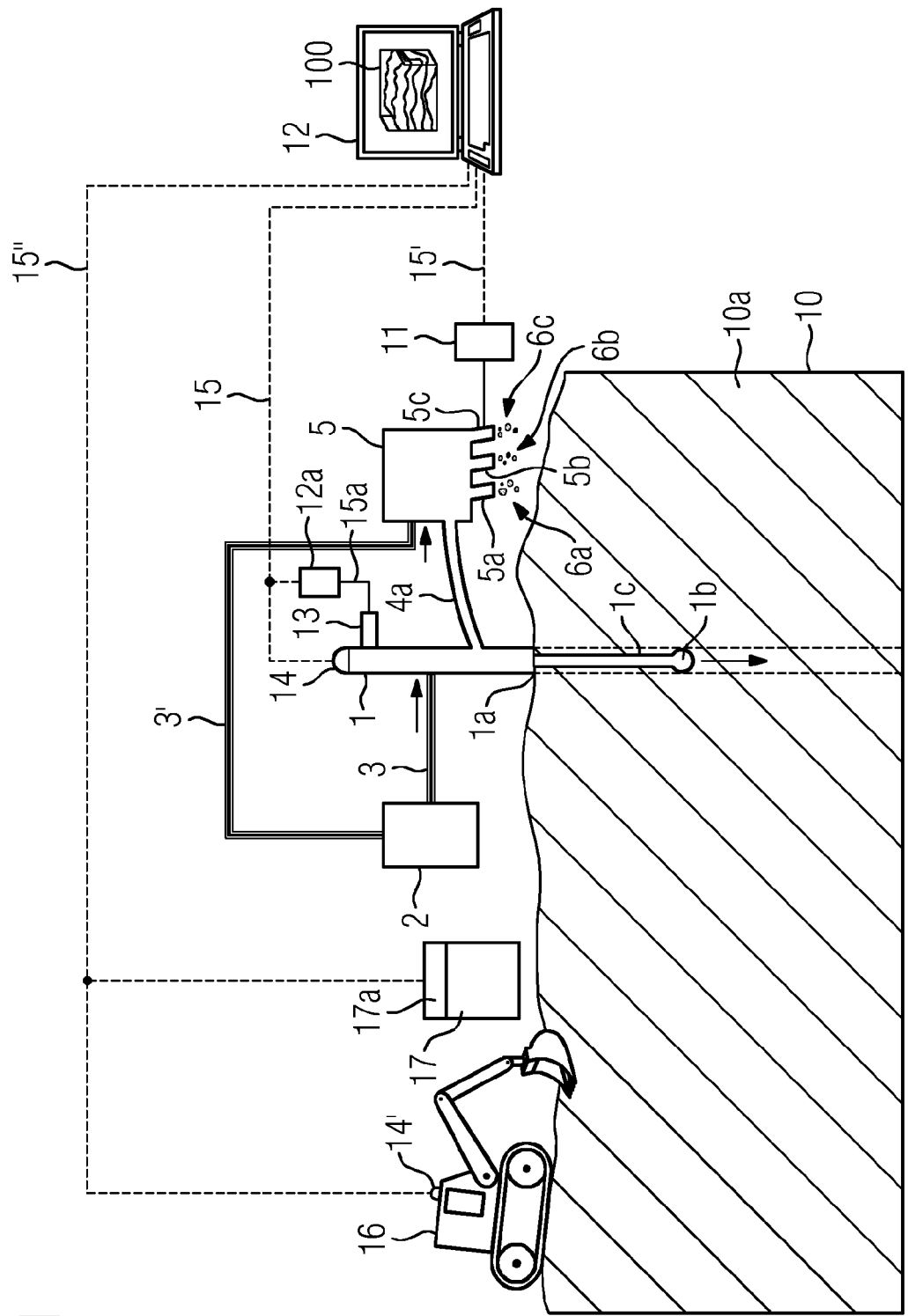
FIG. 1 schematically shows an apparatus for carrying out a method.

Some embodiments provide a method and an apparatus by means of which the yield in a deposit is increased.

For example, some embodiments provide a method for increasing the yield in a deposit comprising a rock which comprises a valuable mineral which is to be exposed as a result of the rock being comminuted, and at least one further mineral, wherein the valuable mineral has a higher density than the at least one further mineral, comprising the following steps:

carrying out a drilling operation using a drilling tool prior to the rock being extracted, drillings being generated in the process, forming an aerosol comprising the drillings and a gas stream, transferring the aerosol from the drilling tool to at least one air separator, carrying out a hydraulic classification, wherein at least two fractions comprising in each case equal-falling particles of the drillings are formed, and determining a property belonging to at least one of the fractions and used as a measure for setting an optimum degree of comminution of the rock.

Other embodiments provide an apparatus for carrying out the disclosed method, comprising at least one comminution machine for comminuting the rock, wherein a degree of comminution of the rock can be changed, at least one control and/or regulating unit for setting the optimum degree of comminution at the at least one comminution machine, at least one drilling tool, at least one unit for providing the gas stream which is connected by way of at least one gas line to the at least one drilling tool, at least one air separator per drilling tool which is connected to the at least one drilling tool by at least one aerosol line, at least one device for determining at least one property of the fractions, and at least one computing unit for acquiring the at least one determined property of the fractions which forms the measure for determining the optimum degree of comminution, and optionally for transmitting at least one manipulated variable, determined on the basis of the measure, to the at least one control and/or regulating unit for setting the optimum degree of comminution at the at least one comminution machine.

Certain embodiments use the knowledge that the properties of drillings which are produced by a drilling tool during a drilling operation have a direct correlation with the grain size of the minerals which are present in the rock which has been drilled through. Targeted evaluation of hydraulically classified fractions of the drillings surprisingly enables sufficiently accurate conclusions to be drawn about the grain sizes present in the rock which has been drilled through and enables fast and uncomplicated determination and setting of the degree of comminution that is optimum for the rock which has been drilled through. An optimum degree of comminution is regarded as a degree of comminution for the respective rock at which comminution is carried out up to exposure of the at least one valuable mineral present, but not beyond.

The method and the device may allow particularly fast and sufficiently accurate adjustment of the degree of comminution to the locally present grain size of the valuable mineral in the rock. The optimum degree of comminution is assigned to the rock which has been drilled through during the drilling operation, such that the data for each drill hole is available on a depth-dependent and timely basis. Instead of the evaluation of the cores obtained during core drilling operations to determine the respective rock structure, the drillings can now simply be analyzed when investigating a deposit. The number of drill holes can be significantly increased since complex laboratory analyses of cores are no longer required. In particular drilling operations to provide blast holes for determining the respective rock structure can also now be used, and these are placed in a narrower grid than for exploration drillings. Blast holes are typically sunk at a horizontal distance of 2 to 5 m, it being possible to provide data with a vertical resolution in the dm range. Particularly fast and accurate deposit modeling, and consequently particularly efficient extraction of the deposit, is thus possible.

Since there is a slight time difference between the drillings being produced and the evaluation of the properties of the hydraulically classified fractions of the drillings, primarily due to the existing conveying line of the aerosol between drill bit and air separator, this difference must of course be taken into account during modeling in order to be able to assign the correct mineral grain size locally, and consequently the optimum degree of comminution, to the rock.

In one embodiment of the method the property is determined in that a particle size analysis is carried out on the equal-falling particles of the fractions, with two particle fractions having different mean particle sizes being obtained in at least one of the fractions, the fractions being separated from one another by gap grading, wherein the particle sizes d of a first particle fraction are proportional to a local grain size of the valuable mineral in the rock and are used as a measure for setting the optimum degree of comminution of the rock.

The particle size distribution in the hydraulically classified fractions of the drillings is in direct correlation to the grain size of the minerals which are present in the rock which has been drilled through. Targeted evaluation, in particular of the particle size distribution of a hydraulically classified fraction of the drillings, surprisingly enables sufficiently accurate conclusions to be drawn about the mineral grain sizes present in the rock which has been drilled through.

In the case where particle size analyses of at least two fractions exhibit gap grading in each case, the first particle fraction which originates from the fraction in which the gap grading is greatest, or in which the distance between the mean particles sizes of the particle fractions is greatest, is used as a measure.

In general it is currently regarded as necessary for the method for the valuable mineral in the rock to exhibit at least 1.5 times the density of the further mineral. With lower density differences, no particle fractions which can be clearly distinguished from one another or evaluated are yielded in the particle size analysis of one of the fractions of the drillings obtained following hydraulic classification.

An ore mineral may be exposed as the valuable mineral by comminution of the rock. "Ores" are designated as naturally occurring mineral aggregates of economic interest from which one or more reusable materials can be extracted by machining. In most cases these are minerals which to a greater or lesser extent contain metal components, such as iron, copper, nickel, tin, zinc, silver, gold, etc.

In one embodiment of the method the particle size analysis of the selected fraction is performed automatically using an optical analysis, e.g., using laser diffraction. In this case the particles of the chosen fraction are optically counted and measured. In particular the equal-falling particles of the chosen fraction are optically analyzed continuously during their fall, for example directly at the corresponding discharge channel for the fraction at the air separator. The result of the analysis therefore has a particularly close time correlation with drilling at a certain position in the rock and, with knowledge of the conveying speed of the drillings from the drill bit to the air separator and to the optical analysis, can easily be taken into account computationally. Alternatively a screen analysis, for example, of a hydraulically classified fraction of the drillings is also possible for carrying out particle size analysis. This procedure is much slower, however.

It may be advantageous if a depth of a drill bit of the drilling tool and/or position data concerning the position of the drilling tool in the deposit is acquired during the drilling operation and are logically linked to the measure, determined at this location, for setting the optimum degree of comminution, and that rock extracted at this location is comminuted in accordance with the determined measure.

Extremely accurate deposit modeling is possible with knowledge of the grain size distribution, present in all three dimensions of the deposit, of the at least one valuable mineral in the deposit, and this has been explained already in the introduction. To determine the current position of the drilling tool during a drilling operation in the deposit as accurately as possible, the gradient of the drill hole in particular is measured and the position of the drilling starting point is acquired, e.g., using at least one GPS unit.

The apparatus may also comprise an extraction tool for extracting the rock and/or for conveying rock which has already been coarsely pre-comminuted in a blast, and which likewise comprises at least one GPS unit.

The position data of an extraction tool may be transmitted by a wireless data transmission to the at least one computing unit. The extraction tool for extracting the rock can be formed by a discontinuous excavator, in particular a shovel or flat excavator, or a continuous excavator, such as a bucket wheel excavator or chain-and-bucket excavator, or the like.

An extraction tool for conveying rock which has already been coarsely pre-comminuted by a blast can be formed by a wheel loader. The liberated or dislodged rock is conventionally managed by way of a material supply system in which the position or storage location of the blasted rock is stored and by way of which the wheel loader can be controlled. The extracted or blasted rock is, optionally after intermediate storage, given up to dump trucks or conveyor belts and conveyed to the at least one comminution machine or conveyed directly into the at least one comminution machine where further comminution of the rock takes place until the valuable mineral is exposed.

At least one predefined drilling parameter and at least one measured value characterizing a current drilling behavior of the drilling tool may be acquired at the drilling tool. A dependency of the at least one measured value on the at least one drilling parameter is then eliminated computationally and at least one resulting rock-texture-dependent characteristic value is used as a further measure for setting an optimum degree of comminution of the rock. This improves the accuracy of mineral grain size analysis, and consequently determination of the optimum degree of comminution.

The at least one drilling parameter is formed for example from a pressure of the drill bit of the drilling tool, a rotational speed of the drill bit, a drill bit material, a gas volume flow of the gas stream, an impact frequency of the drill bit and the like. The impact frequency is yielded inter alia from pressure and gas stream data.

The at least one measured value characterizing the current drilling behavior is chosen in particular from the group of measured values comprising a drilling speed, a resulting torque at the top drive of the drill bit, a gas pressure of the gas stream, an energy input into the drilling tool, a vibration behavior of a drill pipe of the drilling tool, and the like.

The drilling speed for example is therefore dependent inter alia on the strength and composition of the rock which has been drilled through, high strength and/or an accumulation of hard minerals leading to a reduction in the drilling speed. However, the drilling speed is also dependent on which drilling tool and drilling device is used. The type, geometry and state of wear of the drill bit are important in particular here. These drilling parameters are obviously to be taken into account when assessing the drilling speed.

The at least one computing unit of the apparatus is connected using data communication links to the at least one device. This is taken to mean either a connection using cabling, but in particular a wireless radio link. Wireless data transmission to the at least one computing unit enables the computing unit to be arranged spatially separated from the drilling operations so as to be protected from dust and vibrations.

The at least one computing unit of the apparatus may also be configured to acquire the at least one drilling parameter or the at least one measured value at the drilling tool characterizing the current drilling behavior of the drilling tool. Sensors provided on the drilling tool may be used for this purpose or additional sensors may be attached to the drilling tool.

The at least one computing unit is also advantageously configured to computationally eliminate a dependency of the at least one measured value, characterizing a current drilling behavior of the drilling tool, on the at least one drilling parameter and to calculate the at least one rock-texture-dependent characteristic value which constitutes a further measure for the local grain size of the valuable mineral. Computational elimination of the dependency on the drilling parameters requires a manageable number of preliminary tests in which the individual influencing variables are determined and correlated with one another. The database created in this way is stored on the at least one computing unit and is used to determine the characteristic value dependent solely on the texture of the rock.

The at least one computing unit may also be configured to determine the manipulated variable on the basis of the measure and the further measure. The optimum degree of comminution can be chosen even more accurately as a result.

The determined property of the hydraulically classified fractions of the drillings is not used simply as a measure for determining an optimum degree of comminution and for setting the same, however. It can also be used generally to control the extraction operation. In particular the data is also used to control a blast operation and/or a conveying operation and/or a material management operation in the region of the deposit. A quantity of explosive for example can therefore be adjusted locally to the composition and strength of the rock, the extracted rock being selectively managed in accordance with its properties, in particular with respect to storage and transport, it being possible to use a suitable material management system. This increases the efficiency of the extraction operation and saves energy besides. The at least one computing unit is configured in particular to control extraction operation accordingly.

The at least one air separator and the at least one device for determining at least one property of the fractions, in particular for carrying out a particle size analysis, may be arranged in the immediate vicinity of the drilling tool, in particular on the drilling tool. The time for conveying the drillings from the site of origin to the air separator and the required analysis time are minimized as a result. A cross-flow air separator may be used as the air separator.

In one embodiment of the apparatus at least one structure-borne noise sensor for acquiring a measured value, characterizing the current drilling behavior, in the form of a vibration behavior of the drill pipe of the drilling tool, is present on the at least one drilling tool. The properties of the rock which is currently being drilled through, may therefore be deduced from the vibration of the drill pipe.

FIG. 1 schematically shows an apparatus for carrying out a method in the region of a deposit 10 with rock 10*a* shown in section. The rock 10*a* comprises a valuable mineral in the form of chalcopyrite and a further mineral in the form of quartz, the valuable mineral having a density which is at least 1.5 times higher than the further mineral. In the region of a drilling starting point 1*a* the apparatus comprises a drilling tool 1 with a drill bit 1*b* and a drill pipe 1*c* and a unit 2 for providing a gas stream to form an aerosol 4 together with the drillings 7, 8 produced at the drill bit 1*b* (cf. also FIG. 3). The unit 2 for providing a gas stream is connected to the drilling tool 1 by way of at least one gas line 3.

Starting from the drilling starting point 1*a*, a drilling operation is carried out in the rock 10*a* using the drilling tool 1, the drillings 7, 8 comprising particles 7 of valuable mineral and particles 8 of the further mineral. Introducing the gas stream using the unit 2 by way of a gas line 3 into the drilling tool 1 in the direction of the drill bit 1*b* causes the drillings 7, 8 to be conveyed away from the drill bit 1*b*. A free-flowing aerosol 4 is formed from the drillings 7, 8 and the gas stream, and this is conveyed counter to the drilling direction to the earth's surface.

The apparatus also comprises an air separator 5 which is connected to the drilling tool 1 by way of an aerosol line 4*a*. The aerosol 4 is led via the aerosol line 4*a* from the drilling tool 1 to the air separator 5, here in the form of a cross-flow air separator, and a hydraulic classification is carried out in the gas stream 9, with the drillings 7, 8 being segmented into three fractions 6*a*, 6*b*, 6*c*. These each comprise equal-falling particles of the drillings 7, 8, i.e. in fraction c for example there are both small particles 1' of valuable mineral and much larger particles 8' of the further mineral with a lower density which, owing to the same sink rate, are carried away to the same distance by the gas stream 9.

The apparatus also comprises a device 11 for determining a property of the fractions 6*a*, 6*b*, 6*c* of the drillings 7, 8 formed at the air separator 5. Each fraction 6a, 6b, 6b comprises equal-falling particles of the drillings 7, 8 in each case, i.e. in fraction 6c for example there are both small particles 1' of valuable mineral and much larger particles 8' of the further mineral with a lower density which, owing to the same sink rate, are carried away to the same distance by the gas stream 9.

Here the device 11 is an optical analysis unit for carrying out a particle size analysis on the equal-falling particles of the fractions 6a, 6b, 6c in the respective discharge chute 5a, 5b, 5c of the air separator 5.

The device 11 carries out a particle size analysis on all three fractions 6a, 6b, 6c. This can take place sequentially but may be carried out simultaneously for all three fractions 6a, 6b, 6c which trickle from the discharge chutes 5a, 5b, 5c of the air separator 5. The device 11 is connected to a computing unit 12 by data communication links, a data transmission 15' e.g., taking place wirelessly.

Figure 3:
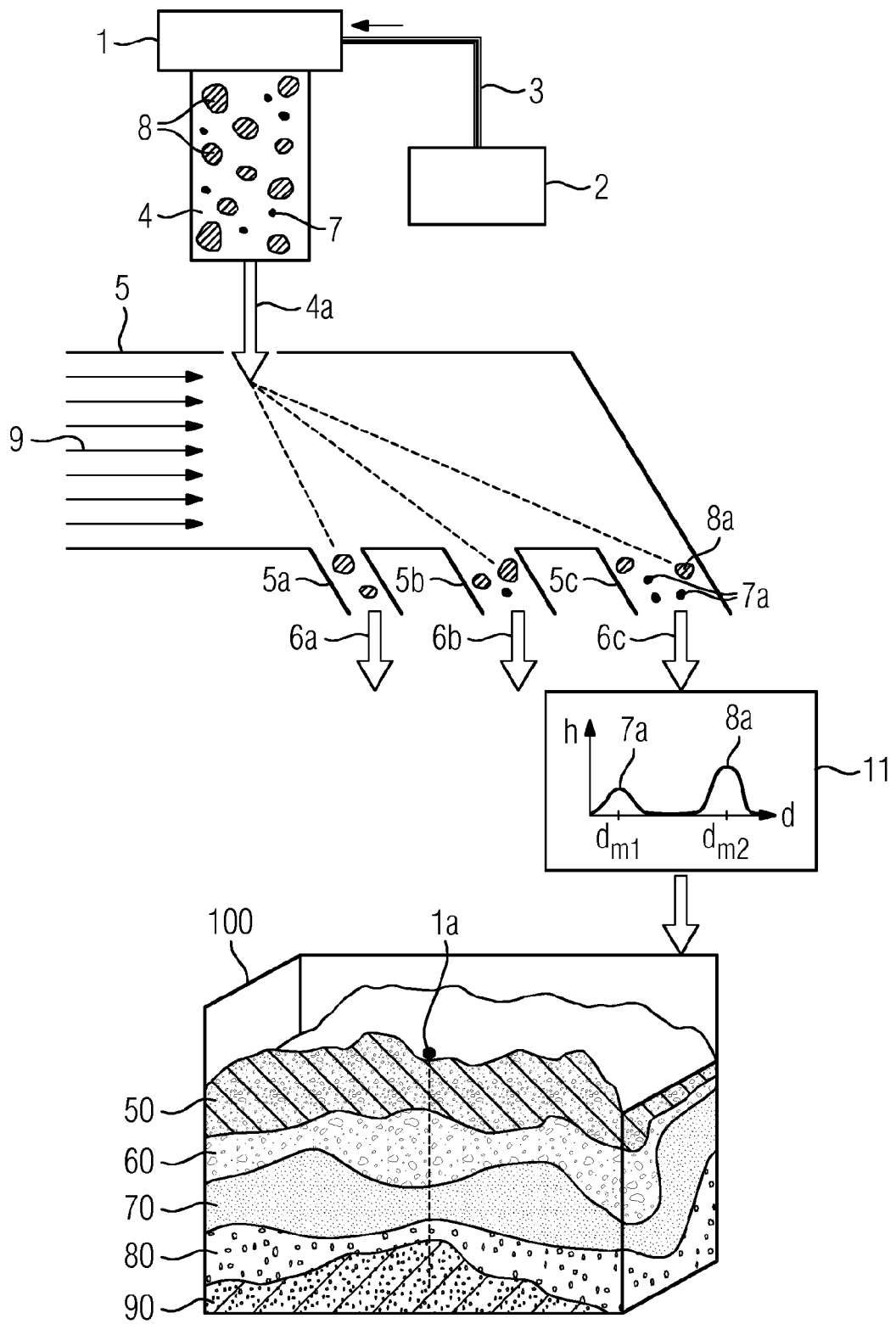
FIG. 3 schematically shows a sequence of the method.

FIG. 3 shows the procedure for the fraction 6c by way of example, which trickles from discharge chute 5c of the air separator 5.

A frequency h of particles per particle size d or particle diameter is determined. Two particle fractions 7a, 8a having different mean particle sizes $d_{m1}$, $d_{m2}$ result which are separate from one another here due to gap grading. Gap grading is in this case taken to mean a region in which there are no particles of certain particle sizes.

The particle size analysis of the fraction in which the distance between the two particle fractions is maximal is now evaluated further. The region of gap grading is accordingly particularly large here. It is accordingly assumed that the fraction 6c fulfills this condition in this case.

The particle size d of the first particle fraction 7a of the fraction 6a is proportional to the local grain size of the valuable mineral in the rock 10a and is consequently used as a measure for the—depth-dependent—optimum degree of comminution of the rock 10a in this local region.

The particle size analyses determined by the device 11 can either be evaluated in the device 11 and the evaluation transmitted to the computing unit 12, or the computing unit 12 takes over the evaluation. During the evaluation the particle fractions of each fraction 6a, 6b, 6c are analyzed and that fraction is chosen in which there is a distance between a first particle fraction 7a and a second particle fraction 7b and this distance is maximal.

The device 11 and/or the computing unit 12 are/is therefore used to acquire the particle sizes of the determined particle fractions and to correlate these with a local grain size of the valuable mineral in the rock 10a.

To be able to identify the drilling starting point 1a of the drilling tool 1 in the deposit 10 the drilling tool 1 has at least one GPS unit 14. The position data, in particular the current depth of the drill bit 1b and the drill hole gradient and at least one measured value, characterizing the current drilling behavior, such as the drilling speed, are transmitted in particular by radio 15 to the computing unit 12 which is positioned so as to be spatially separate from the drilling operations.

According to FIG. 1 the apparatus also comprises an extraction tool 16 for extracting the accumulated rock 10a, and this also has a GPS unit 14'. The position data of the extraction tool 16 is transmitted in particular by a data transmission 15" via radio to the computing unit 12. The extraction tool 16 is in this case formed either by a discontinuous excavator, in particular a shovel or flat excavator, or by a continuous excavator, such as a bucket wheel excavator or chain-and-bucket excavator, or the like.

The extraction tool 16 directly or indirectly passes the locally extracted rock 10a to a comminution machine 17 which comprises a control and/or regulating unit 17a for setting the optimum degree of comminution. According to the extraction site of the rock 10a, which is known to the computing unit 12 owing to the GPS unit 14' on the extraction tool 16, a manipulated variable for the optimum degree of comminution is transmitted to the comminution machine 17 or its control and/or regulating unit 17a, e.g., from the computing unit 12 by a data transmission 15" via radio, as a function of the mineral grain size previously determined at this extraction site and the extraction depth. Of course this can also be carried out on site by an operator, however.

The optimum degree of comminution is in this case predefined by the computing unit 12 or the operator in such a way that the valuable mineral is exposed. The comminution machine 17 now comminutes the rock 10a following appropriate setting of its comminution tool in accordance with the optimum degree of comminution predefined in each case. Almost complete separation of the exposed valuable mineral from the further mineral can now take place, with the result that efficient exploitation of the deposit 10 is realized.

A structure-borne noise sensor 13 may also be installed on the drilling tool 1 and this is used for acquiring a measured value, characterizing the current drilling behavior, in this case the vibration behavior of the drill pipe 1c of the drilling tool 1. With knowledge of the drilling parameters predefined on the drilling tool 1 and the vibration behavior of the drill pipe 1c, a dependency of the vibration behavior on the drilling parameters can be computationally eliminated using a further computing unit 12a which is arranged in the vicinity of the drilling tool 1. A rock-texture-dependent characteristic value results which can also be used as a further measure for a local grain size of the valuable mineral and also in particular the strength of the rock.

The data concerning the vibration behavior is so extensive that a data transmission thereof via radio to the computing unit 12 may only be achieved with difficulty. However, an evaluation of the vibration data, made in a further computing unit 12a installed locally, can be transmitted via radio from the further computing unit 12a to the remotely arranged computing unit 12.

Figure 2:
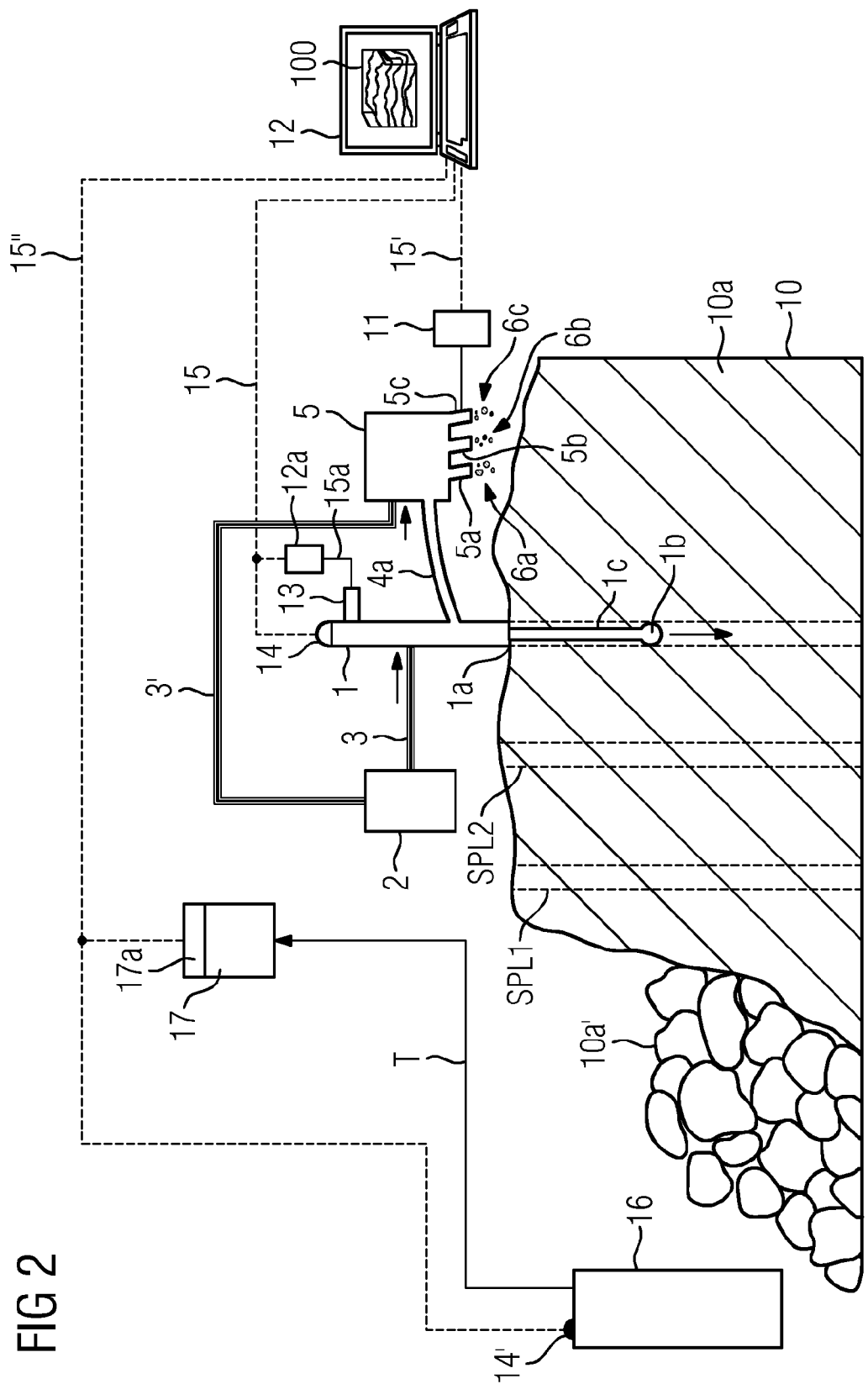
FIG. 2 schematically shows a further apparatus for carrying out a method.

FIG. 2 schematically shows a further apparatus for carrying out a method in the region of a deposit 10 with rock 10a shown in section. Reference numerals identical to those in FIG. 1 denote identical elements.

In contrast to FIG. 1, the rock 10a is in this case provided with blast holes SPL1, SPL2 which the drilling tool 1 has formed. A number of blast holes may be introduced in the rock 10a at a horizontal distance of 2 to 5 m. The rock 10a is liberated from the accumulated rock 10a by a blast, the coarsely precomminuted rock 10a' then being received by an extraction tool 16, for example in the form of a wheel loader. Having been recorded by way of a material management system, and therefore retrievable again, it can now be temporarily stored or be conveyed directly to the comminution machine 17 (see arrow T).

From the determined local grain sizes of the valuable mineral an appropriate or optimum degree of comminution is determined for the rock and assigned locally to the rock. During a subsequent extraction of the rock 10a the extracted material is stored in accordance with the grain size of the valuable mineral present or thereafter the comminution machine 17 is controlled and/or regulated accordingly for the corresponding material, the operator or the computing unit 12 communicating a corresponding manipulated variable, for setting the optimum degree of comminution, to the control and/or regulating unit 17a of the comminution machine 17.

A deposit model 100 can be created on the basis of the determined mineral grain sizes of the rock at the various drilling sites in the deposit 10, and in particular also at different depths of the drill bit in the rock, with an appropriately high number of drilling sites or blast holes, and this model reproduces a sufficiently accurate three-dimensional image of the deposit 10. The spatial position 50, 60, 70, 80, 90 of rock with different local grain sizes of the valuable mineral can be seen in the deposit model 100. Five rock layers, located at different depths, with valuable minerals with different grain sizes, were determined proceeding from drilling starting point 1a.

Figure 4:
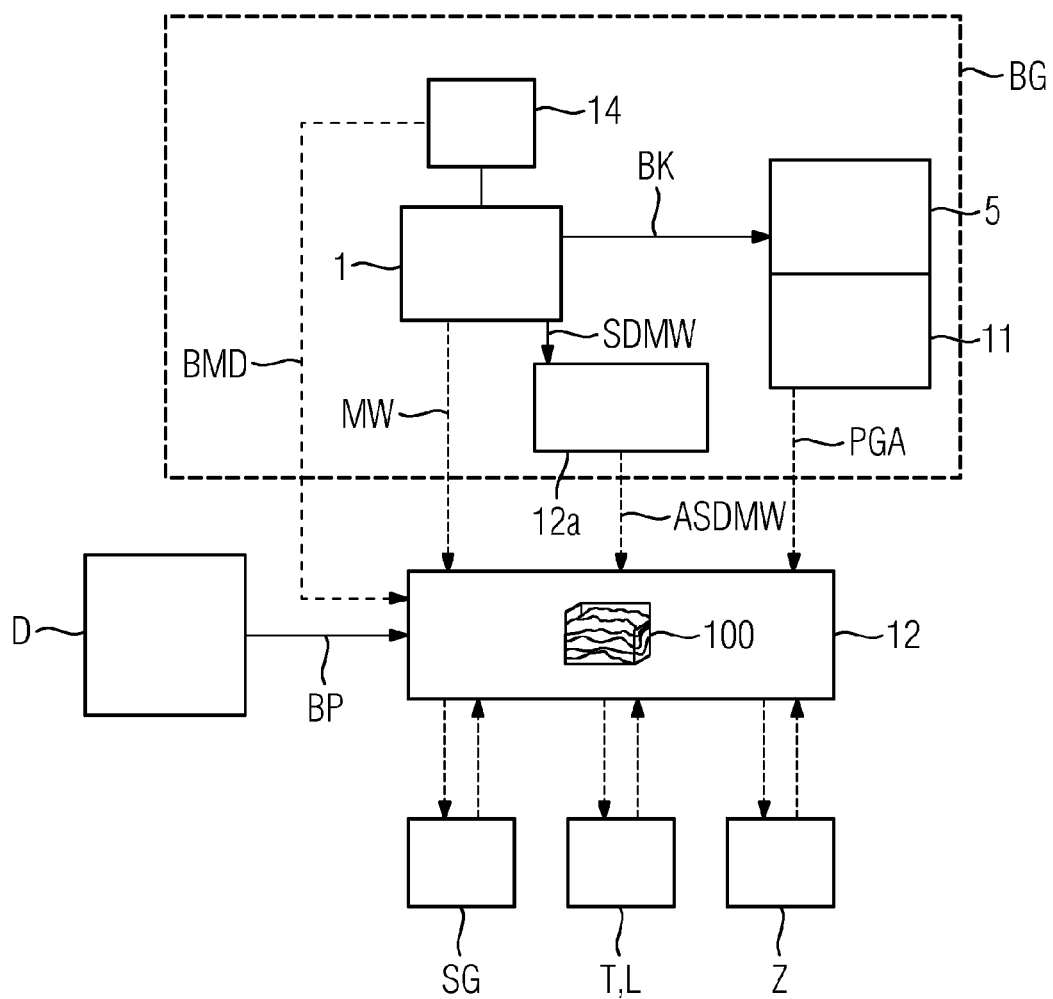
FIG. 4 schematically shows the possible data and material flows for a method.

FIG. 4 schematically shows data and material flows for a possible method. The computing unit 12 is supplied via a data source D with the (typically known) drilling parameters BP, it being possible for the operator and/or other electronic equipment to be used as the data source. Drilling parameters BP in the form of data concerning the type of drilling tool 1, the type and geometry of the drill bit of the drilling tool 1, the period of use during which the drill bit has already been operating, the pressure and/or rotational speed of the drill bit, etc. are transmitted. As a rule a wired data line is used here. During the drilling operation current measured values MW characterizing the drilling behavior are transmitted to the computing unit 12 by the drilling tool 1 or measured value sensors present thereon. The measured values MW are for example a drilling speed, an energy input into the drilling tool 1, etc. The current position data BMD of the drilling tool 1, in particular the drill bit, is also transmitted to the computing unit 12 by the GPS unit 14.

The drillings BK produced by the drilling tool are transferred to the air separator 5 following formation of the aerosol and are hydraulically classified. The fractions issuing from the discharge chutes of the air separator 5 are analyzed with respect to the particle size distributions present therein in each case by the at least one device 11. The analysis data PGA determined is transferred to the computing unit 12, optionally after a further evaluation in the device 11 with respect to the fraction with maximum gap grading.

Once the measured values MW, position data BMD and particle size analysis PGA have been recorded in the region of the drilling operation BG, these are transmitted, e.g., wirelessly (see broken lines), to the computing unit 12 which is arranged spatially separately therefrom.

Measured values MW relating to the drilling behavior, which are present in the form of vibration data SDMW, are evaluated in the further computing unit 12a directly in the region of the drilling operations BG and are then transmitted wirelessly to the computing unit 12.

The extraction operation in the region of the deposit 100 is then controlled on the basis of the model 100 determined in the computing unit 12, and primarily with respect to a blast SG, conveying T and storage L of the extracted rock as well as rock comminution Z. Thus, for example, with knowledge of the model 100, and optionally the local strength of the rock, the locally used quantity of explosive can be adjusted, the extracted rock stored at different locations according to property, wherein rock with the same grain size of the valuable mineral in particular is combined, conveyed in the desired sequence to the comminution machine and comminuted there to different degrees as a function of the grain size of the valuable mineral.

FIGS. 1 to 4 merely illustrate examples of the apparatus and method. The person skilled in the art is easily capable of adapting the disclosed apparatus and method to the respective deposit in order to determine the local grain sizes of the valuable minerals present and to determine the degree of comminution appropriate thereto for the respective rock. Therefore, depending on the deposit, drilling into the ground can of course also be carried out vertically and/or horizontally and/or diagonally. A different type of air separator and/or other types of device for particle size analysis may also be used. Thus, for example, it is also possible to carry out a sieve classification of the hydraulically classified fractions into the individual particle fractions, although this is time-consuming.

The invention claimed is:

1. A method for increasing the yield in a deposit comprising a rock which comprises a valuable mineral to be exposed by a comminution of the rock, and at least one further mineral, wherein the valuable mineral has a higher density than the at least one further mineral, the method comprising:
performing a drilling operation using a drilling tool prior to an extraction of the rock, wherein the drilling operation generates drillings,
forming an aerosol comprising the drillings and a gas stream,
transferring the aerosol from the drilling tool to at least one air separator,
performing a hydraulic classification of the drillings into at least two fractions, each comprising equal-falling particles of the drillings,
determining a property belonging to at least one of the fractions, and
setting a target degree of comminution of the rock based on the determined property.

2. The method of claim comprising comminuting the rock to expose an ore mineral as the valuable mineral.

3. The method of claim 1, comprising performing a particle size analysis on the equal-falling particles of the fractions,
wherein in at least one of the fractions at least two particle fractions with different mean particle sizes are obtained which are separated from one another by gap grading,
wherein the particle sizes of a first particle fraction are proportional to a local mineral grain size of the valuable mineral in the rock and are used as a measure for setting the optimum degree of comminution of the rock.

4. The method of claim 3, wherein if the particle size analyses indicate that at least two fractions exhibit gap grading, the particle sizes of the first particle fraction are used as a measure which originates from the fraction in which gap grading is the greatest.

5. The method of claim 3, wherein the particle size analysis is performed using an optical analysis.

6. The method of claim 5, wherein the optical analysis of the equal-falling particles of the fractions is performed during the fall of the particles.

7. The method of claim 1, comprising:
acquiring and logically linking to the measure for setting the optimum degree of comminution of the rock at least one of (a) a depth of a drill bit of the drilling tool and (b) position data concerning the position of the drilling tool in the deposit during the drilling operation.

8. The method of claim 1, comprising acquiring at least one predefined drilling parameter and at least one measured value characterizing a current drilling behavior of the drilling tool, and
wherein at least one resulting rock-texture-dependent characteristic value is used as a further measure for setting the optimum degree of communication of the rock.

9. The method of claim 8, wherein the at least one drilling parameter comprises at least one of a pressure of a drill bit of the drilling tool, a rotational speed of the drill bit, a gas volume flow of the gas stream for forming the aerosol, an impact frequency of the drill bit, a previous period of use of the drill bit, and material or geometric data of the drill bit.

10. The method of claim 8, comprising selecting the at least one measured value characterizing the current drilling behavior from a group of measured values consisting of a drill speed, a resulting torque on a top drive of a drill bit, a gas pressure of the gas stream for forming the aerosol, an energy input into the drilling tool, and a vibration behavior of a drill pipe of the drilling tool.

11. The method of claim 1, wherein the determined property is also used to control at least one of a blasting operation, a conveying operation, and a material management operation in the region of the deposit.

12. An apparatus for increasing the yield in a deposit comprising a rock which comprises a valuable mineral to be exposed by a comminution of the rock, and at least one further mineral, wherein the valuable mineral has a higher density than the at least one further mineral, the apparatus comprising:
at least one comminution machine configured to comminute the rock according to a selectable degree of comminution of the rock,
at least one control unit configured to set a target degree of comminution at the at least one comminution machine,
at least one drilling tool configured to perform a drilling operation that generates drillings,
at least one unit configured to deliver a gas stream via at least one gas line to the at least one drilling tool to form an aerosol comprising the gas stream and the drillings generated by the drilling operation,
at least one air separator per drilling tool, the at least one air separator connected to the at least one drilling tool by at least one aerosol line via which the aerosol is transferred to the at least one separator,
wherein the at least one separator is configured to perform a hydraulic classification of the drillings into at least two fractions of the drillings, each comprising equal-falling particles of the drillings,
at least one device configured to determine at least one property of at least one of the fractions of the drillings, and
at least one computing unit programmed to calculate at least one manipulated variable based on the at least one property of the at least one of the fractions of the drillings, and
wherein the at least one control unit is configured to set the target degree of comminution at the at least one comminution machine based on the calculated at least one manipulated variable.

13. The apparatus of claim 12, wherein the at least one computing unit is further configured to acquire at least one drilling parameter of the at least one drilling tool and at least one measured value at the drilling tool characterizing a current drilling behavior of the drilling tool.

14. The apparatus of claim 13, wherein the at least one computing unit is further programmed to:
computationally eliminate a dependency of the at least one measured value, characterizing the current drilling behavior of the drilling tool, on the at least one drilling parameter of the at least one drilling tool to calculate at least one rock-texture-dependent characteristic value, and
calculate the at least one manipulated variable based on (a) the at least one property of the at least one of fraction of drillings and (b) the at least one rock-texture-dependent characteristic value.

15. The apparatus of claim 12, wherein the at least one computing unit is further configured to use the determined property additionally to control at least one of a blasting operation, a conveying operation, and a material management operation in the region of the deposit.

16. The apparatus of claim 12, wherein the at least one air separator and the at least one device for determining the at least one property of the at least one of the fractions of the drillings are arranged in the immediate vicinity of the drilling tool.

17. The apparatus of claim 12, wherein the at least one air separator comprises a cross-flow separator.

18. The apparatus of claim 12, comprising at least one structure-borne noise sensor on the at least one drilling tool for detecting a vibration behavior of a drill pipe of the drilling tool.

19. The apparatus of claim 12, further comprising an extraction tool, and wherein at least one of the drilling tool and the extraction tool comprises a GPS unit.

* * * * *